United States Patent [19]

Haruna et al.

[11] Patent Number: 4,619,958

[45] Date of Patent: Oct. 28, 1986

[54] MIXED 2,2,6,6-TETRAMETHYL PIPERIDINYL CARBOXYLIC ACID ESTER AND AMIDE LIGHT STABILIZERS AND STABILIZED SYNTHETIC POLYMERS

[75] Inventors: Tohru Haruna, Okegawa; Atsushi Nishimura, Saitama, both of Japan

[73] Assignee: Adeka Argus Chemical Co., Ltd., Urawa, Japan

[21] Appl. No.: 537,479

[22] Filed: Sep. 30, 1983

[30] Foreign Application Priority Data

Oct. 2, 1982 [JP] Japan .................. 57-173589

[51] Int. Cl.$^4$ .................................... C08K 5/34
[52] U.S. Cl. .................... 524/102; 524/103; 546/19; 546/188
[58] Field of Search ............ 524/102, 103; 536/19, 536/188

[56] References Cited

U.S. PATENT DOCUMENTS

| | | | |
|---|---|---|---|
| 3,640,928 | 2/1972 | Murayama et al. | 524/102 |
| 4,102,858 | 7/1978 | Minagawa et al. | 546/188 |
| 4,136,081 | 1/1979 | Minagawa et al. | 524/102 |
| 4,344,877 | 8/1982 | Nickles et al. | 524/103 |

*Primary Examiner*—John Kight
*Assistant Examiner*—Kriellion Morgan

[57] ABSTRACT

Mixed light stabilizers for synthetic polymers are provided having the formula

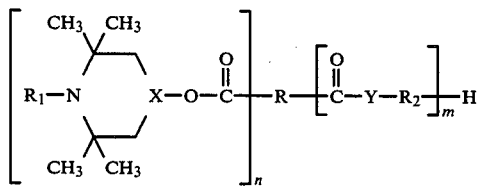

wherein:

R is a polyvalent group selected from the group consisting of aliphatic hydrocarbon groups having from one to about twenty carbon atoms, cycloaliphatic hydrocarbon groups having from three to about sixteen carbon atoms and aromatic hydrocarbon groups having from six to about thirty carbon atoms; such groups substituted with from one to about six groups selected from the group consisting of hydroxy, acyloxy, and halogen; and $N(C_{n_1}H_{2n_1})_3$ where $n_1$ is a number from one to five;

$R_1$ is selected from the group consisting of hydrogen, oxyl, alkyl, epoxy alkyl and hydroxy alkyl having from one to about twelve carbon atoms, alkyl aryl having from six to about eighteen carbon atoms, and acyl having from two to about twelve carbon atoms;

$R_2$ is selected from the group consisting of alkyl and alkenyl having from eight to about thirty carbon atoms;

$R_3$ is lower alkyl having from one to about six carbon atoms;

X is >CH— or

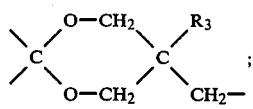

Y is

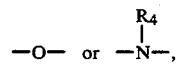

where $R_4$ is hydrogen or $R_2$;
m is a number from 0 to 6; and
n is a number from 3 to 6.

The mixture comprises from about 10 to about 60% by weight of compounds wherein m is 0, and from about 90 to about 40% by weight of compounds wherein m is from 1 to 6.

24 Claims, No Drawings

MIXED 2,2,6,6-TETRAMETHYL PIPERIDINYL CARBOXYLIC ACID ESTER AND AMIDE LIGHT STABILIZERS AND STABILIZED SYNTHETIC POLYMERS

The most important piperidine compounds are the carboxylic acid esters of 2,2,6,6-tetramethyl piperidine-4-ol or ketal of trimethylolalkane with 2,2,6,6-tetramethylpiperidine-4-one, and many ester compounds have been disclosed as light stabilizers.

U.S. Pat. No. 3,640,928, patented Feb. 8, 1972 to Murayama et al discloses piperidine derivative stabilizers for synthetic polymers against photo- and thermo-deterioration having the general formula

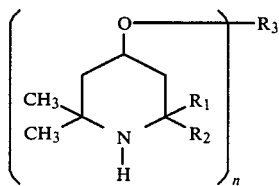

or a salt thereof.

In the above Formula I:

$R_1$ and $R_2$, which may be the same or different, each are an alkyl group such as methyl, ethyl, isopropyl or dodecyl, or they form, together with the carbon atom to which they are attached, a saturated alicyclic group such as

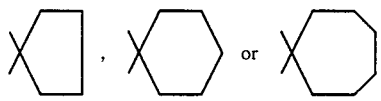

or a group of the formula

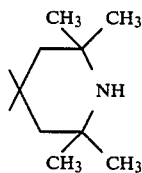

n is an integer of 1 to 3 inclusive; and $R_3$ is an acyl group derived from an aliphatic, alicyclic or heterocyclic mono di or tri carboxylic acid; a mono di or tri N-substituted carbamoyl group derived from an N-substituted carbamic acid; N-substituted thiocarbomoyl group derived from an N-substituted thiocarbamic acid; or a group obtained by removing hydroxyl groups from a mono di or tri oxoacid; an alkyl group; a cycloalkyl group; an aralkyl group; an aryl group; or a group of the general formula

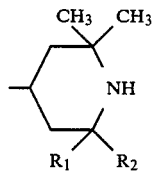

(wherein $R_1$ and $R_2$ are as defined above).

U.S. Pat. No. 3,840,494, patented Oct. 8, 1974 to Murayama et al provides acid esters of 4-piperidinol derivatives having the formula

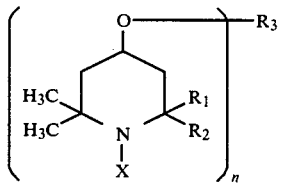

wherein $R_1$ and $R_2$ may be the same or different and represent an alkyl group of 1 to 4 carbon atoms or they may form, together with the carbon atom to which they are attached, a saturated alicyclic group or the group of the formula

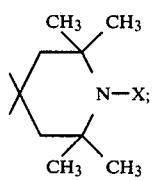

X is hydrogen atom, oxygen free radical (—O) or an alkyl group of 1 to 4 carbon atoms;

n is an integer of 1 through 4 inclusive; and $R_3$ represents, when n is 1, an acyl group derived from an aliphatic or aromatic monocarboxylic acid, when n is 2, a diacyl group derived from an aliphatic or aromatic dicarboxylic acid or carbonyl group, when n is 3, a triacyl group derived from an aliphatic or aromatic tricarboxylic acid or a trivalent group obtained by eliminating three hydroxyl groups from phosphoric acid, phosphorous acid or boric acid, and when n is 4, a tetraacyl group derived from an aromatic tetracarboxylic acid or a tetravalent group obtained by eliminating four hydroxyl group from orthosilicic acid.

These are stabilizers for synthetic polymers against photo- and thermal-deterioration.

U.S. Pat. No. 4,046,737, patented Sept. 6, 1977 to Holt et al provides 1- and 4-substituted piperidine stabilizers for organic materials having the formula:

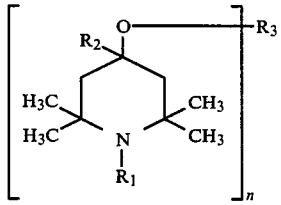

and their salts wherein n is 1, 2, 3 or 4;

$R_1$ is a monovalent residue and is an alkyl residue having from 1 to 20, preferably 1 to 12 carbon atoms, an alkenyl or alkynyl residue having from 3 to 20, preferably 3 to 12 carbon atoms, an aralkyl residue having from 7 to 12 carbon atoms, or a residue having the formula:

$$-(CH_2)_m-\underset{\underset{R_4}{|}}{CH}-X_1$$

or $$-\underset{\underset{R_4}{|}}{CH}-X_2$$

$R_2$ is an alkyl residue having from 1 to 4 carbon atoms, an alkenyl or alkynyl residue having 3 to 20 carbon atoms, preferably 3 to 4 carbon atoms, a cycloalkyl residue having from 5 to 12 carbon atoms, an aryl residue having from 6 to 11 carbon atoms or an aralkyl residue having from 7 to 9 carbon atoms or preferably hydrogen; and $R_3$ is a monovalent divalent or trivalent radical such as $R_1$ or a group obtained by removing hydroxyl groups from a sulphinic acid, a sulphonic acid, a phosphorus containing acid or a boric acid, or $R_3$ is an aryl residue, a cycloalkyl group having from 5 to 12 carbon atoms, or a residue having the formula:

$$R_2\diagup\hspace{-0.3em}\underset{CH_3\hspace{1em}CH_3}{\overset{CH_3\hspace{1em}CH_3}{\diagdown}}\hspace{-0.3em}N-R;$$

wherein $R_1'$ is hydrogen or $R_1'$ has the same significance as $R_1$.

U.S. Pat. No. 4,102,858, patented July 25, 1978 to Minagawa et al provides 2,2,6,6-tetramethyl-4-piperidyl thiocarboxylates and aminocarboxylates having the general formula:

$$[R_1OOC\text{\textendash}Y_1\text{\textendash}(S)_{m3}]_{m1}]_{n1}\text{\textendash}\underset{\underset{Q}{|}}{Z}\text{\textendash}\left[(S)_{m4}\text{\textendash}Y_2\text{\textendash}\left[COO\diagup\hspace{-0.3em}\underset{CH_3\hspace{1em}CH_3}{\overset{CH_3\hspace{1em}CH_3}{\diagdown}}\hspace{-0.3em}NX\right]_{m2}\right]_{n2}$$

wherein:

$m_1$, $m_3$, and $m_4$ are numbers from 0 to 1;
$m_2$ is a number from 1 to 2;
$n_1$ is a number from 0 to 2;
$n_2$ is a number from 0 to 3;
$n_3$ is a number from 0 to 2;
$R_1$ is selected from the group consisting of alkyl, aralky, cycloalkyl and 2,2,6,6-tetramethyl-4-piperidyl;
$R_2$ is selected from the group consisting of alkyl, cycloalkyl, alkylaryl, aralkyl, and hydroxy-substituted such radicals;
$R_1$ and $R_2$ have from one to about twenty carbon atoms;
X is hydrogen or O;
$Y_1$ and $Y_2$ are bivalent linking radicals having from one to about 20 carbon atoms, and selected from the group consisting of alkylene and cycloalkylene; and amino-substituted such radicals;
Q is selected from the group consisting of $SR_2$ and $$\underset{\underset{R_2}{|}}{N}-R_2;$$

Z is an organic radical having a valence from 2 to 4 and from one to about twenty carbon atoms, and selected from the group consisting of alkylene, alkylidene, aralkylene, aralkylidene, alkarylene, alkarylidene, heterocycloalkylene, heterocycloalkylidene, cycloalkylene and cycloalkylidene; amino-substituted such radicals and 2,2,6,6-tetramethyl-4-piperidylidene;

there being from one to four sulfur-containing or nitrogen-containing such groups and at least one $$-Y_2-COO\diagup\hspace{-0.3em}\overset{\diagdown}{\underset{\diagup}{\hspace{2em}}}\hspace{-0.3em}NX\text{ group}$$

attached to the Z radical.

U.S. Pat. No. 4,105,625, patented Aug. 8, 1978 to Minagawa et al provides 2,2,6,6-tetramethyl-4-piperidyl carboxylic acid esters of aliphatic di- or tri-carboxylic acids, useful as light stabilizers for organic polymeric materials, and having the general formula:

$$\left[R_1-O-\underset{\underset{O}{\|}}{C}-\right]_a\underset{\underset{[CH]_m}{|}}{Z}$$

wherein:

$R_1$ is selected from the group consisting of $$HN\diagup\hspace{-0.3em}\underset{CH_3\hspace{1em}CH_3}{\overset{CH_3\hspace{1em}CH_3}{\diagdown}}\hspace{-0.3em}\text{\textemdash and }HN\diagup\hspace{-0.3em}\underset{CH_3\hspace{1em}CH_3}{\overset{CH_3\hspace{1em}CH_3}{\diagdown}}\hspace{-0.3em}\diagup\hspace{-0.3em}\overset{O}{\underset{O}{\diagdown}}\hspace{-0.3em}\underset{CH_2-}{\overset{R_2}{\diagdown}}$$

$R_2$ is $CH_3$ or $C_2H_5$;
a is selected from the group consisting of 2 and 3;
m is selected from the group consisting of 1, 2, 3 and 4; and
Z is a divalent or trivalent aliphatic radical carrying from two to three $$R_1-O-\underset{\underset{O}{\|}}{C}-$$

groups, and can include from one to four hydroxyl groups OH.

U.S. Pat. No. 4,116,927, patented Sept. 26, 1978 to Minagawa et al provides 2,2,6,6-tetramethyl-4-piperidyl carboxylic acid esters of butane or butene tricarboxylic acids, useful as stabilizers for organic polymeric materials, and having the general formula:

$$\begin{array}{c} CH_2-COOR_1 \\ | \\ CH-COOR_1 \\ | \\ R_2=C-COOR_1 \\ | \\ H \end{array}$$

wherein:

$R_1$ is selected from the group consisting of

<chemical structures> the $R_1$ groups can be the same or different;
$R_2$ is selected from the group consisting of $CH_3$ and $CH_2$; and
$R_3$ is lower alkyl.

U.S. Pat. No. 4,136,081, patented Jan. 23, 1979 to Minagawa et al provides 2,2,6,6-tetramethyl-4-piperidyl carboxylic acid esters of aliphatic tetracarboxylic acids, useful as stabilizers for organic polymeric materials, and having the general formula:

$$\left[ \begin{array}{c} R_1-O-C \\ \parallel \\ O \end{array} \right]_a - Z - \left[ \begin{array}{c} C-O-R_2 \\ \parallel \\ O \end{array} \right]_b$$

wherein:

$R_1$ is selected from the group consisting of

<chemical structures> and when a is 2, 3, or 4, the $R_1$ groups can be the same or different;

$R_2$ is selected from the group consisting of hydrogen; alkyl; alkenyl; cycloalkyl; alkcycloalkyl; cycloalkalkyl; aryl; aralkyl; and alkaryl; and when b is 2 or 3, the $R_2$ groups can be the same or different;

$R_3$ is selected from the group consisting of hydrogen and O;

$R_6$ is lower alkyl;

a is selected from the group consisting of 1, 2, 3 and 4;

b is selected from the group consisting of 0, 1, 2 and 3;

a+b is equal to 4; and Z is a tetravalent aliphatic or cycloaliphatic radical carrying four $$\begin{array}{c} R-O-C- \\ \parallel \\ O \end{array} \text{ groups,}$$

where R is $R_1$ or $R_2$, and can include from one to three hydroxyl groups OH.

U.S. Pat. No. 4,212,974, patented July 15, 1980 to Murayama et al provides piperidine derivatives useful as stabilizers for polymeric materials having the formula:

$$\left( \begin{array}{c} CH_3 \quad CH_3 \\ R_1-N \qquad \qquad A-O \\ CH_3 \quad CH_3 \end{array} \right)_{R_2}$$

wherein $R_1$ represents hydrogen atom, an alkyl group, a substituted alkyl group, an alkenyl group, an alkynyl group, a substituted or unsubstituted aralkyl group, an aliphatic acyl group, an alkoxycarbonyl group or an aralkoxycarbonyl group, n is an integer of 1 to 4; when n is 1, $R_2$ represents hydrogen atom, an aliphatic, aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, a N-substituted carbamoyl group, a N-substituted thiocarbamoyl group, a monovalent group from an oxoacid or group $$\begin{array}{c} -C=CH-COOR_4 \\ | \\ R_3 \end{array}$$

in which $R_3$ represents hydrogen atom, a lower alkyl group or phenyl group and $R_4$ represents an alkyl group; when n is 2, $R_2$ represents carbonyl group, an aliphatic or aromatic diacyl group, an alkylene group, an alkenylene group, an alkynylene group, an aralkylene group, a N-substituted dicarbamoyl group or a divalent group from an oxoacid; when n is 3, $R_2$ represents an aromatic triacyl group or a trivalent group from an oxoacid; and when n is 4, $R_2$ represents an aromatic tetraacyl group, and A represents a group $$\begin{array}{c} -CH_2 \quad R_5 \\ \diagdown \diagup \\ C \\ \diagup \diagdown \\ -CH_2 \quad CH_2- \end{array}$$

in which $R_5$ represents hydrogen atom or a lower alkyl group or, when n is 1, $R_5$ represents together with $R_2$ a group

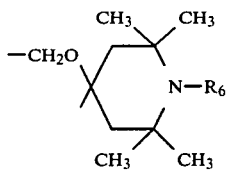

in which $R_6$ represents the same group as defined in $R_1$ and may be the same or different from $R_1$, or a group

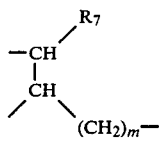

in which n is 1 or 2 and $R_7$ represents hydrogen atom or, when n and m are 1, $R_7$ represents methylene group together with $R_2$.

U.S. Pat. No. 4,312,804, patented Jan. 26, 1982 to Minagawa et al provides 2,2,6,6-tetraalkyl-4-piperidyl alcohol esters of tetradecylene polycarboxylic acids, useful as light stabilizers for organic polymeric materials, and having the general formula:

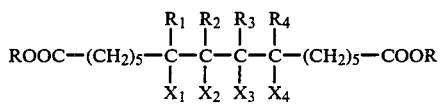

in which
R is selected from the group consisting of

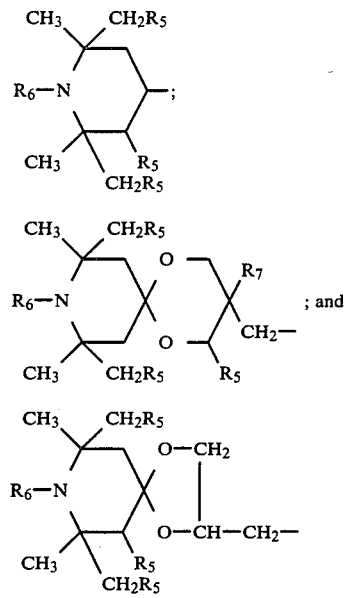

wherein:
$R_5$ and $R_6$ are each hydrogen or lower alkyl or hydroxyalkyl having from one to about six carbon atoms;
$R_7$ is lower alkyl having from one to about six carbon atoms;

$R_1$, $R_2$, $R_3$ and $R_4$ are selected from the group consisting of hydrogen and methyl;
$X_1$ and $X_3$ are selected from the group consisting of hydrogen and COOR;
$X_2$ and $X_4$ are selected from the group consisting of COOR and

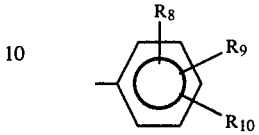

wherein
$R_8$, $R_9$, and $R_{10}$ are selected from the group consisting of hydrogen, hydroxy, alkyl, and alkoxy having from one to about eighteen carbon atoms.

Many of these compounds are unstable to hydrolysis. Moreover, many of these compounds are powders of high melting point, and consequently are difficult to disperse in the polymer composition. If a liquid is required, a solution has to be formed, for example, for use as a stabilizer for coatings, and it is necessary to employ large amounts of solvent due to low solubility of the compound in the common solvents.

Japan Kokai No. 82-111335 discloses liquid mixtures of bis(piperidyl) dicarboxylates and mono-piperidyl-mono-loweralkyl-di-carboxylates. However, although these mixtures do not crystallize at low temperatures, the hydrolytic stability is not improved, and the volatility of the stabilizers is still too high.

In accordance with the present invention, there are provided mixed carboxylic acid esters and amides of 2,2,6,6-tetramethylpiperidines with polycarboxylic acids having from three to six carboxylic acid groups having improved hydrolytic stability and solubility due to the presence therein of esterifying higher alcohol groups or amido higher groups.

These mixed esters and amides have the formula:

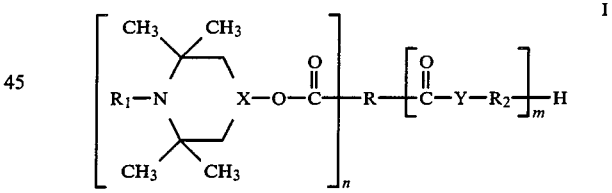

wherein:
R is a polyvalent group selected from the group consisting of aliphatic hydrocarbon groups having from one to about twenty carbon atoms, cycloaliphatic hydrocarbon groups having from three to about sixteen carbon atoms and aromatic hydrocarbon groups having from six to about thirty carbon atoms; such groups substituted with from one to about six groups selected from the group consisting of hydroxy, acyloxy, and halogen; and $N(C_{n_1}H_{2n_1})_3$ where $n_1$ is a number from one to five;
$R_1$ is selected from the group consisting of hydrogen, oxyl, alkyl, epoxy alkyl and hydroxy alkyl having from one to about twelve carbon atoms, alkyl aryl having from six to about eighteen carbon atoms, and acyl having from two to about twelve carbon atoms;
$R_2$ is selected from the group consisting of alkyl and alkenyl having from eight to about thirty carbon atoms;

$R_3$ is lower alkyl having from one to about six carbon atoms;

X is >CH— or

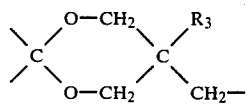

Y is $$-O- \text{ or } -\underset{|}{\overset{R_4}{N}}-,$$

where $R_4$ is hydrogen or $R_2$;
m is a number from 0 to 6; and
n is a number from 3 to 6.

The mixture comprises from about 10 to about 60% by weight of compounds wherein m is 0, and from about 90 to about 40% by weight of compounds wherein m is from 1 to 6.

These mixtures are excellent light stabilizers for synthetic polymers, and the invention accordingly also includes synthetic polymer compositions having an improved resistance to deterioration upon exposure to light due to the presence of a sufficient amount of such mixtures.

Exemplary $R_1$ alkyl include methyl, ethyl, isopropyl, propyl, butyl, isobutyl, sec-butyl, amyl, isoamyl, hexyl, heptyl, octyl, 2-ethyl hexyl, isononyl, nonyl, decyl, isodecyl, undecyl and dodecyl;

Exemplary $R_1$ alkylaryl include benzyl;

Exemplary $R_1$ hydroxyalkyl include 2-hydroxyethyl, 2-hydroxypropyl, 2-hydroxybutyl, phenethyl, phenpropyl, trimethyl benzyl, nonyl benzyl, and decyl benzyl;

Exemplary $R_1$ epoxyalkyl include 2,3-epoxypropyl.

Exemplary $R_1$ acyl include acetyl, propionyl, butyroyl, octanoyl, acetoxyethyl, propionyloxyethyl, acryloyl, methacryloyl and benzoyl;

Exemplary $R_2$ alkyl include octyl, 2-ethylhexyl, isooctyl, nonyl, isononyl, decyl, isodecyl, dodecyl, 2-methylundecyl, tridecyl, 2-methyldodecyl, tetradecyl, 2-methyltridecyl, hexadecyl, 2-hexyldecyl, octadecyl, eicosyl, docosyl, tetracosyl, 2-decyltetradecyl, 2-decylpentadecyl, 2-undecyltetradecyl, 2-undecylpentadecyl and triacontyl;

Exemplary $R_2$ alkenyl include decenyl, dodecenyl, tetradecenyl, hexadecenyl and octadecenyl;

Exemplary $R_3$ lower alkyl include methyl, ethyl, propyl, isopropyl, butyl, isobutyl, amyl, isoamyl and hexyl.

R is the residue of a polycarboxylic acid of the formula $R-(COOH)_n$ where R is aliphatic, aromatic, or nitrilo

Exemplary polycarboxylic acids include tricarballylic acid, citric acid, acetyl citric acid, butane-1,2,3-tricarboxylic acid, 3-butene-1,2,3-tricarboxylic acid, trimellitic acid, butane-1,2,3,4-tetracarboxylic acid, 1,1,2,2-ethenetetracarboxylic acid, 7-bicyclo[2.2.2]octene-2,3,5,6-tetracarboxylic acid, 1,1,2,3-propanetetracarboxylic acid, pyromellitic acid, 1,6,7,8,9,14-tetradecanehexacarboxylic acid, 1,6,8,14-tetradecanetetracarboxylic acid, nitrilotriacetic acid and nitrilotripropionic acid.

The mixed esters and amides of Formula I can be easily prepared by the reaction of a lower alkyl ester of the corresponding polycarboxylic acid with a mixture of

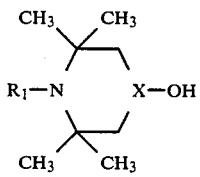

and $R_2$—Y—H, or by the reaction of a lower alkyl ester of the corresponding polycarboxylic acid with

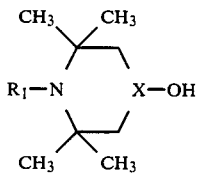

(or $R_2$—Y—H), followed by $R_2$—Y—H (or

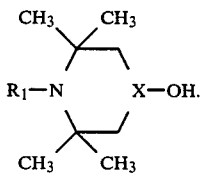

They can also be prepared by simply mixing a compound of Formula I where m is 0 with one or more compounds of Formula I where m is 1 to 6.

The following examples illustrate the synthetic (as opposed to simple mixing) procedure.

EXAMPLE I

Tetramethyl-butane-1,2,3,4-tetracarboxylate 8.7 g, 2,2,6,6-tetramethyl-4-piperidinol 15.5 g, tetra-isopropyltitanate 0.5 g and PEGASOL 3040 (Mobil Oil; aliphatic hydrocarbon solvent) 25 ml were heated and stirred for 6 hours at 160°–165° C. under a stream of nitrogen.

Then, 2-hexyl-decanol 8.0 g and tetra-iso-propyltitanate 0.1 g were added and the mixture heated and stirred at 160°–165° C. for an additional four hours. The reaction mixture was washed with water and dried, and the solvent was distilled off under vacuum. A pale brown liquid was obtained.

The product was analyzed using high speed liquid chromatography (HLC), and the following composition determined:

Stabilizer No. 1

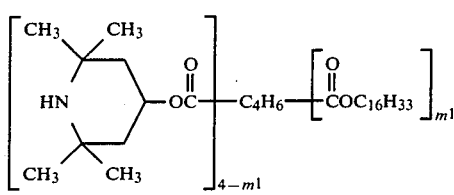

Species of compound of above Formula where $m^1$ is:

| $m^1$ | % by weight |
|---|---|
| 0 | 28 |
| 1 | 58 |
| 2 | 14 |
| 3 | 0 |

EXAMPLE II

Tetrakis(2,2,6,6-tetramethyl-4-piperidyl)butane-1,2,3,4-tetracarboxylate 15.8 g, stearyl alcohol 5.4 g, tetra-iso-propyltitanate 0.4 g and PEGASOL 3040 25 ml were heated and stirred at 160°–165° C. for 2 hours under a stream of nitrogen, and then an additional 2 hours at 160°–165° C. under reduced pressure. The reaction mixture was washed with water and dried, and the solvent was distilled off under vacuum. A white waxy solid was obtained.

The product was analyzed with HLC and had following composition.

Stabilizer No. 2

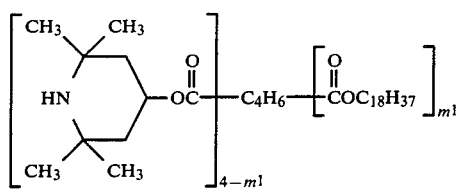

Species of compound of above Formula where $m^1$ is:

| $m^1$ | % by weight |
|---|---|
| 0 | 24 |
| 1 | 50 |
| 2 | 26 |
| 3 | 0 |

Using the same procedure, the stabilizers shown below were obtained:

TABLE A

| Stabilizer No. | State | R | n | $R_1$—N group (2,2,6,6-tetramethylpiperidyl with $R_1$) | —Y—$R_2$ | Weight % of Species of Formula I where m=0 | m=1 | m=2 | m=3 |
|---|---|---|---|---|---|---|---|---|---|
| 3 | Liquid | —CH$_2$CHCHCH$_2$— | 4 | $R_1$ = HN (2,2,6,6-tetramethyl-4-piperidyl) | —O—CH$_2$CHC$_8$H$_{17}$, with C$_6$H$_{13}$ branch | 17 | 38 | 33 | 12 |
| 4 | Liquid | —CH$_2$CHCHCH$_2$— | 4 | $R_1$ = CH$_3$N (2,2,6,6-tetramethyl-4-piperidyl) | —O—CH$_2$CHC$_8$H$_{17}$, with C$_6$H$_{13}$ branch | 30 | 59 | 11 | 0 |
| 5 | Liquid | —CH$_2$CHCHCH$_2$— | 4 | $R_1$ = CH$_3$N (2,2,6,6-tetramethyl-4-piperidyl) | —O—CH$_2$CHC$_8$H$_{17}$, with C$_6$H$_{13}$ branch | 19 | 39 | 34 | 8 |
| 6 | Liquid | —CH$_2$CHCHCH$_2$— | 4 | $R_1$ = HN (2,2,6,6-tetramethyl-4-piperidyl) | —O—C$_{13}$H$_{27}$(iso) | 29 | 58 | 13 | 0 |

TABLE A-continued

| Stabilizer No. | State | R | n | R₁—N(with piperidine ring having CH₃ CH₃ / CH₃ CH₃ and X—) | —Y—R₂ | Weight % of Species of Formula I where m=: m=0 | m=1 | m=2 | m=3 |
|---|---|---|---|---|---|---|---|---|---|
| 7 | Liquid | $-CH_2CHCHCH_2-$ | 4 | HN-piperidine (2,2,6,6-tetramethyl) | $-O-C_{12\sim15}H_{25\sim31}$*¹ | 28 | 57 | 15 | 0 |
| 8 | Liquid | $-CH_2CHCHCH_2-$ | 4 | HN-piperidine (2,2,6,6-tetramethyl) | $-O-(CH_2)_8CH=CHC_8H_{17}$ | 27 | 55 | 18 | 0 |
| 9 | Wax | $-CH_2CHCHCH_2-$ | 4 | HN-piperidine spiro ketal with $C_2H_5$, $CH_2-$ | $-O-C_{18}H_{37}$ | 27 | 50 | 23 | 0 |
| 10 | Liquid | $-CH_2CHCH_3$ | 3 | HN-piperidine (2,2,6,6-tetramethyl) | $-O-C_{13}H_{27}(iso)$ | 43 | 42 | 14 | 1 |
| 11 | Liquid | $-CH_2CHCH_3$ | 3 | CH₃N-piperidine spiro ketal with $C_2H_5$, $CH_2-$ | $-O-CH_2CHC_8H_{17}$ with $C_6H_{13}$ | 32 | 47 | 19 | 2 |
| 12 | Wax | $+CH_2\!\!\rightarrow_5\!+CH\!\!\rightarrow_4\!+CH_2\!\!\rightarrow_5\!-$ | 6 | HN-piperidine (2,2,6,6-tetramethyl) | $-O-C_{18}H_{37}$ | 25 | 40 | 27 | 8 |
| 13 | Liquid | $N+CH_2\!\!\rightarrow_3$ | 3 | CH₃N-piperidine (2,2,6,6-tetramethyl) | $-O-CH_2-CHC_8H_{17}$ with $C_6H_{13}$ | 42 | 43 | 14 | 1 |

*¹C₁₂–C₁₅ mixed alcohol (DOBANOL 25; Mitsubishi Chemical Ind. Ltd.)

EXAMPLE III

Tetramethyl-butane-1,2,3,4-tetracarboxylate 14.5 g, stearyl amine 13.5 g and acetic acid 1 g were heated at 160° C. for 12 hours. Toluene 100 ml was added, and the reaction mixture washed with water and dried. The toluene was distilled off. 2,2,6,6-Tetramethyl-4-piperidinol 25.9 g, tetra-isopropyltitanate 1.0 g and PEGASOL 3040 40 ml was added and heated and stirred at 160°–165° C. for 12 hours, and an additional 6 hours under reduced pressure. The reaction mixture was washed with water and dried, and the solvent was distilled off. A waxy solid was obtained.

The product was analyzed using HLC, with following results:

Stabilizer No. 14

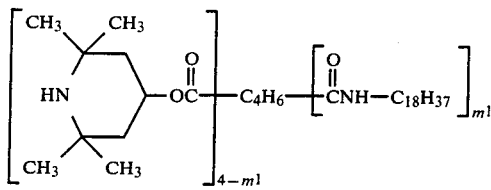

Species of compound of about Formula where $m^1=$:

| $m^1$ | % by weight |
|---|---|
| 0 | 27 |
| 1 | 50 |
| 2 | 23 |
| 3 | 0 |

EXAMPLE IV

Using the same procedure as in Example III, a waxy solid citric ester/amide mixture having the following composition was obtained:

Stabilizer No. 15

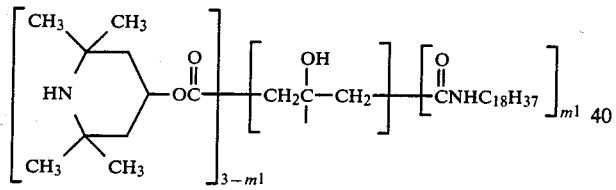

Species of compound of above Formula were $m^1=$:

| $m^1$ | % by weight |
|---|---|
| 0 | 32 |
| 1 | 51 |
| 2 | 17 |
| 3 | 0 |

EXAMPLE V

Tetramethyl-butane-1,2,3,4-tetracarboxylate 8.7 g, 1,2,2,6,6-pentamethyl-4-piperidinol 13.0 g, isotridecanol 11.2 g, tetraisopropyltitanate 0.7 g and PEGASOL 3040 30 ml were heated and stirred for 160° C. for 6 hours, and then an additional 3 hours under reduced pressure. The reaction mixture was washed with water, and dried. The solvent was distilled off. A pale brown liquid was obtained.

The product was analyzed using HLC, with the following results:

Stabilizer No. 16

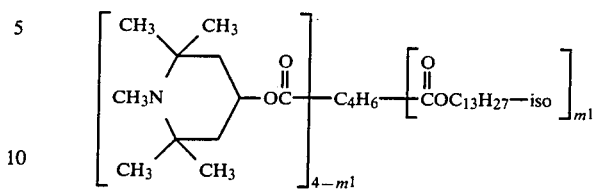

Species of compound of above Formula when $m^1=$:

| $m^1$ | % by weight |
|---|---|
| 0 | 11 |
| 1 | 33 |
| 2 | 38 |
| 3 | 18 |

Small amounts of the stabilizer of this invention when combined with synthetic resin improve the light stability of the resin. The amount of the stabilizer is generally within the range from about 0.001 to about 5 parts by weight, preferably from about 0.01 to about 3 parts by weight, per 100 parts by weight of resin.

Synthetic resins that can have their resistance to deterioration enhanced with hindered bisphenol diphosphonites according to this invention include α-olefin polymers such as polyethylene, polypropylene, polybutene-1, poly-3-methylbutene-1, and copolymers thereof, such as copolymers of ethylene, propylene and butene-1 with each other and with other copolymerizable mixtures thereof, such as ethylenevinyl acetate copolymer; ethylene-propylene copolymer; polystyrene; polyvinyl acetate; polyacrylic esters; copolymers from styrene and another monomer (for example, maleic anhydride, butadiene, and acrylonitrile); acrylonitrilebutadiene-styrene copolymer, acrylic acid ester-butadiene-styrene copolymer, methacrylic acid ester-butadiene-styrene copolymer, polymethacrylate esters such as polymethacrylate; polyvinyl alcohol; polyvinyl formal; polyvinyl butyral; polyphenyleneoxides; linear polyesters such as polyethyleneterephthalate and polybutyleneterephthalate; polyamides such as polycaprolactam and polyhexamethyleneadipamide; polycarbonates; polyacetals; polyurethanes; cellulosic resins; phenol-formaldehyde resins; urea-formaldehyde resins; melamine-formaldehyde resins; epoxy resins; unsaturated polyester resins; silicone resins; halogen-containing resins such as polyvinyl chloride, polyvinyl bromide, polyvinyl fluoride, polyvinylidene chloride, polyvinylidene fluoride, and copolymers thereof, chlorinated polyethylene, chlorinated polypropylene, copolymers of vinylchloride with other copolymerizable monomers such as vinyl acetate, ethylene, propylene, styrene, isobutene, vinylidene chloride, maleic anhydride, acrylonitrile, butadiene, isoprene, acrylic esters and maleic esters; and rubbers such as polyisoprene rubber, polybutadiene rubber, epichlorohydrin rubber, chloroprene rubber, chlorinated rubber and blends of any of the above.

The mixed 2,2,6,6-tetraalkyl piperidyl light stabilizers of the invention can be combined with conventional heat stabilizers such as phenolic antioxidants, polyvalent metal salts of organic acids, organic phosphites, thioethers, and other known heat stabilizers, thereby constituting light and heat stabilizer compositions of the invention.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

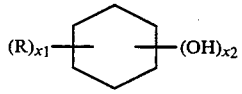

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl.

$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

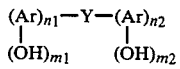

wherein

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

where R' is aryl, alkyl or cycloalkyl, or thiohydrocarbon groups having from one to about thirty carbon atoms, and carboxyl

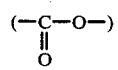

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

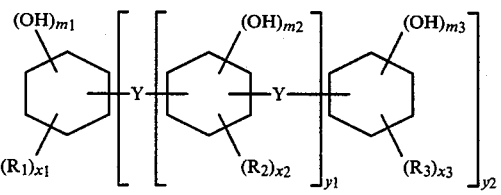

wherein $R_1$, $R_2$ and $R_3$ are inert substituent groups as described in the previous paragraph;

$m_1$ and $m_3$ are integers from one to a maximum of five;

$m_2$ is an integer from one to a maximum of four;

$x_1$ and $x_3$ are integers from zero to four, and $x_2$ is an integer from zero to three;

$y_1$ is an integer from zero to about six and $y_2$ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as: —CH$_2$—CH$_2$—; —(CH$_2$)$_5$—; —CH$_2$—;

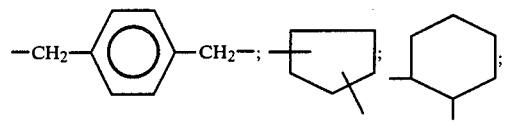

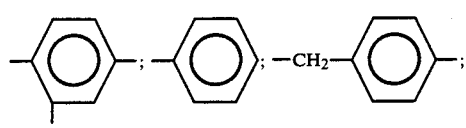

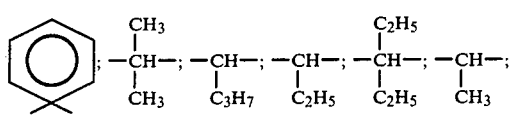

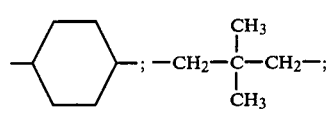

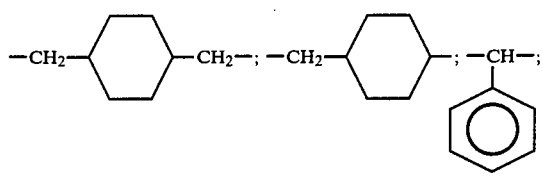

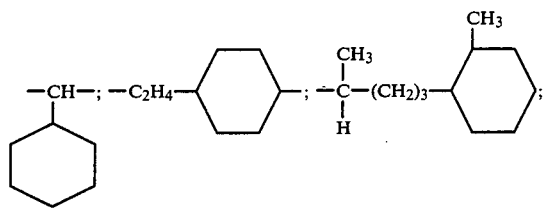

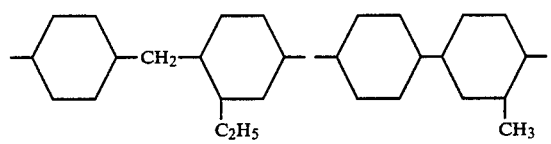

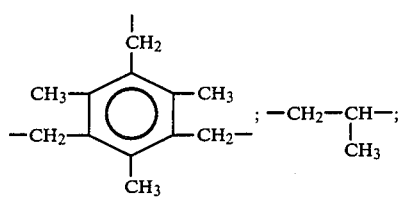

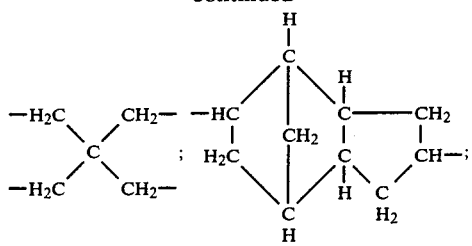

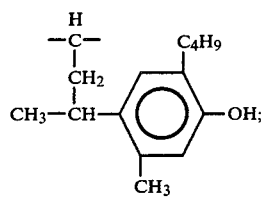

(2) Y groups where only atoms other than carbon link the aromatic rings, such as —O—, —S—,

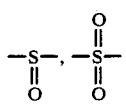

and —(S)$_x$— where x is a number from one to ten;

(3) Y groups made up of more than a single atom including both carbon and other atoms linking the aromatic nuclei, such as: —CH$_2$—O—CH$_2$—;

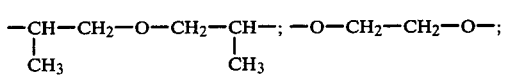

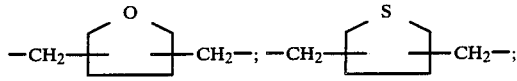

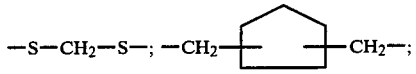

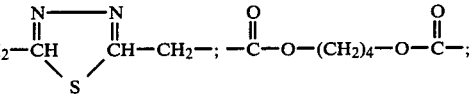

C[—CH$_2$OOCCH$_2$CH$_2$—]$_4$≡;

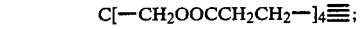

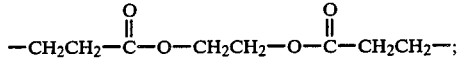

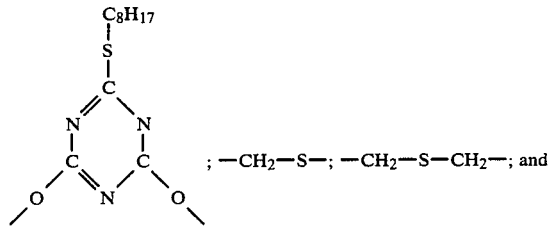

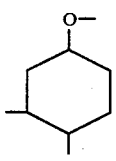

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenyl-phenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m-tert-butyl-p-hydroxy-anisole, p-n-decyloxy-phenol, p-n-decyloxy-cresol, nonyl-n-decyloxy-cresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-dichlorobenzoyl-aminophenol, p-hydroxysalicyl anilide, stearyl-(3,5-di-methyl-4-hydroxy-benzyl)thioglycolate, stearyl-β-(4-hydroxy-3,5-di-t-butylphenyl)propionate, distearyl-3,5-di-t-butyl-4-hydroxybenzylphosphonate, and distearyl(4-hydroxy-3-methyl-5-t-butyl)benzylmalonate.

Exemplary polyhydric phenols are orcinol, propyl gallate, catechol, resorcinol, 4-octyl-resorcinol, 4-dodecylresorcinol, 4-octadecyl-catechol, 4-isooctyl-phloroglucinol, pyrogallol, hexahydroxybenzene, 4-isohexylcatechol, 2,6-ditertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4-hydroxy phenyl)-propane, methylene-bis-(p-cresol), 4,4'-benzylidene bis(2-tertiary-butyl-5-methyl-phenol), 4,4'-cyclo-hexylidene bis-(2-tertiary-butylphenol), 2,2'-methylene-bis-(4-methyl-6-(1'-methyl-cyclohexyl)-phenol), 2,6-bis-(2'-hydroxy-3'-tertiary-butyl-5'-methyl-benzyl)-4-methylphenol, 4,4'-bis-(2-tertiary-butyl-5-methyl-phenol), 2,2'-bis-(4-hydroxy-phenyl)butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol; 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methylphenol), 2,2'-methylene-bis-(4-methyl-6-(1'-methyl-cyclohexyl)-phenol), 4,4'-cyclohexylene bis-(2-tertiary-butyl-phenol), 2,6-bis-(2'-hydroxy-3'-t-butyl-5'-methyl-benzyl)-4-methyl-phenol, 4,4'-oxobis(naphthalene-1,5-diol), 1,3'-bis-(naphthalene-2,5-diol)propane, and 2,2'-butylene bis-(naphthalene-2,7-diol), (3-methyl-5-tert-butyl-4-hydroxyphenyl)-4'-hydroxy-phenyl)propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'-hydroxyphenyl)ethane, (2-hydroxy-phenyl)-(3',5'-di-tert-butyl-4',4-hydroxyphenyl)ethane, 2,2'-methylene-bis-(4-octylphenol), 4,4'-propylene-bis-(2-tert-butyl-phenol), 2,2'-isobutylene-bis-(4-nonylphenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis-(3-t-butyl-4-hydroxyphenyl)thiazolo-(5,4-d)thiazole, 2,2'-bis-(3-methyl-5-t-butyl-4-hydroxyphenyl)thiazolo-(5,4-d)-thiazole, 4,4'-bis-(4-hydroxyphenyl)pentanoic acid octadecyl ester, cyclopentylene-4,4'-bis-phenol, 2-ethylbutylene-4,4'-bisphenol, 4,4'-cyclooctylene-bis-(2-cyclohexylphenol), β,β-thiodiethanol-bis-(3-tert-butyl-4-hydroxyphenoxy acetate), 1,4-butanedio-bis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl)sulfide, bis-(2-tert-butyl-4-hydroxy-5-methylphenyl)sulfide, bis-(2-tert-butyl-4-hydroxy-5-methylphenyl)sulfoxide, bis-(3-ethyl-5-tert-butyl-4-hydroxybenzyl)sulfide, bis-(2-hydroxy-4-methyl-6-tert-butyl-phenyl)sulfide, 4,4'-bis-(4-hydroxyphenol)pentanoic acid octadecyl thiopropionate ester, 1,1,3-tris-(2'-methyl-4-hydroxy-5'-tert-butylphenyl)butane, 1,1,3-tris-(1-methyl-3-hydroxy-4-tert-butylphenyl)butane, 1,8-bis-(2-hydroxy-5-methyl-benzoyl-n-octane, 2,2'-ethylene-bis-[4'-(3-tert-butyl-4-hydroxyphenyl)-thiazole], 1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-hydroxy-3-t-butylphenyl)butyric acid] glycol ester, 4,4'-butylidene-bis-(6-t-butyl-m-cresol), 1,1,3-tris-(2-methyl-4-hydroxy-5-t-butylphenyl)butane, 1,3,5-tris-(3,5-di-t-butyl-4-hydroxybenzyl)-2,4,6-trimethylbenzene, tetrakis [methylene-3(3,5-di-t-butyl-4-hydroxyphenyl)propionate] methane, 1,3,5-tris-(3,5-di-t-butyl-4-hydroxybenzyl)isocyanurate, 1,3,5-tris-(3,5-di-t-butyl-4-hydroxyphenyl)propionyl-oxyethyl isocyanurate, 2-octylthio-4,6-di-(4-hydroxy-3,5-di-t-butyl)phenoxy-1,3,5-triazine, 4,4'-thiobis-(6-t-butyl-m-cresol) and pentaerythritol hydroxyphenyl propionate.

A particularly desirable class of polyhydric polycyclic phenols are the dicyclopentadiene polyphenols, which are of the type:

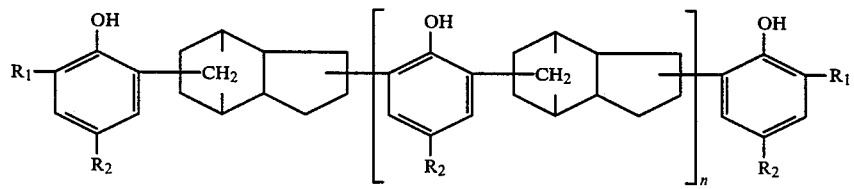

in which

R₁ and R₂ are lower alkyl, and can be the same or different, and n is the number of the groups enclosed by the brackets, and is usually from 1 to about 5. These are described in U.S. Pat. No. 3,567,683, dated Mar. 2, 1971 to Spacht.

A commercially available member of this class is Wingstay L, exemplified by dicyclopentadiene tri-(2-tert-butyl-4-methyl-phenol) of the formula:

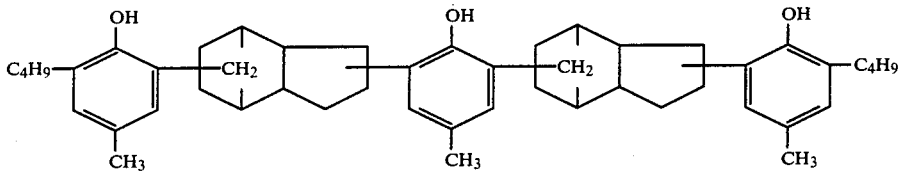

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see e.g., U.S. Pat. No. 3,124,555, U.S. Pat. No. 3,242,135, and British Pat. No. 961,504.

When the stabilizer composition is used in conjunction with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophisphites.

The organic triphosphites in which the radicals are monovalent radicals can be defined by the formula:

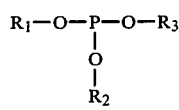

in which $R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

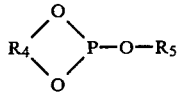

in which $R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$;

$R_5$ is hydrogen or a cation, in the case of the acid phosphites.

Also useful organic triphosphites are mixed heterocyclic-open chain phosphites of the type:

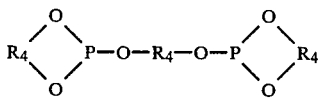

More complex triphosphites are formed from trivalent organic radicals, of the type:

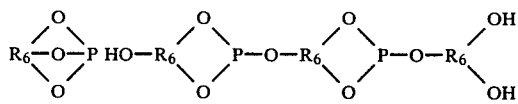

in which $R_6$ is a trivalent organic radical of any of the types of $R_1$ to $R_5$, inclusive, as defined above.

A particularly useful class of complex triphosphites are the tetraoxadiphosphaspiro undecanes of the formula:

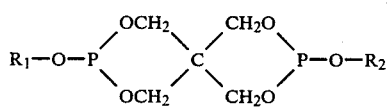

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula:

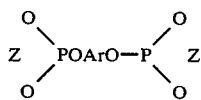

or

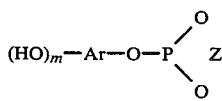

in which

Ar is a mono or bicyclic aromatic nucleus and m is an integer of from 0 to about 5. Z is one or a plurality of organic radicals as defined above for $R_1$ to $R_6$, taken singly or together in sufficient number to satisfy the valences of the two phosphite oxygen atoms.

One or both Z radicals is also hydrogen, in the case of the acid phosphites, and can include additional bicyclic aromatic groups of the type $(HO)_m$—Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl)phosphite, trioctadecyl phosphite, triisooctyl phosphite, tridodecyl phosphite, isooctyl diphenyl phosphite, diisooctyl phenyl phosphite, tri(t-octylphenyl) phosphite, tri-(t-nonylphenyl)phosphite, benzyl methyl isopropyl phosphite, butyl dicresyl phosphite, isooctyl di(octylphenyl)phosphite, di(2-ethylhexyl)(isooctylphenyl)phosphite, tri(2-cyclohexylphenyl)phosphite), tri-α-naphthyl phosphite, tri(phenylphenyl)phosphite, tri(2-phenylethyl)phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane(diphenyl-pentaerylthritol diphosphite), 3,9-di(decyloxy)-2,4,8,10-tetraoxa-3,9-diphosphaspiro (5,5)-undecane, 3,9-di(isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphasprio-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane- 3,9-di-(butoxyethoxyethyloxy)-2,4,8,10-tetraoxa-3,9-diphosphaspiro-(5,5)-undecane, 3,9-di(methoxyethoxyethoxyethyloxy)-2,4,8,10-tetraoxa-3,9-diphosphaspiro-(5,5)-undecane, 3,9-di(methoxy(polyethoxy)ethyloxy)-2,4,8,10-tetraoxa-3,9-diphosphaspiro-(5,5)-undecane where the (polyethoxy)ethyloxy group has an average molecular weight of 350),3,9-di(methoxy(polyethoxy)ethyloxy)-2,4,8,10-tetraoxa-3,9-diphosphaspiro-(5,5)-undecane (where the (polyethoxy)ethyloxy group has an average molecular weight of 550).

Exemplary of the bis aryl triphosphites are: bis(4,4'-thio-bis(2-tertiary-butyl-5-methyl-phenol))isooctyl phosphite, mono(4,4'-thio-bis(2-tertiary-butyl-5-methylphenol))di-phenyl phosphite, tri-(4,4'-n-butylidene-bis(2-tertiary-butyl-5-methylphenol))phosphite, (4,4'-benzylidene-bis(2-tertiary-butyl-5-methyl-phenol)-)diphenyl phosphite, isooctyl 2,2'-bis(-parahydroxyphenyl)propane phosphite, decyl 4,4'-n-butylidene-bis(2-tertiary-butyl-5-methylphenol)phosphite, tri-4,4'-thio-bis(2-tertiary-butyl-5-methylphenol)phosphite, 2-ethylhexyl-2,2'-methylene-bis(4-methyl-6,1'-methylcyclohexyl)phenol phosphite, tri(2,2'-bis-(para-hydroxyphenyl)propane)phosphite, tri(4,4'-thio-bis(2-tertiary-butyl-5-methyl-phenol)phosphite, isooctyl(2,6-bis(2'-hydroxy-3,5-dinonylbenzyl)-4-nonyl phenyl))phosphite, tetra-tridecyl-4,4'-n-butylidene-bis(2-tertiary-butyl- 5-methylphenyl)diphosphite, tetra-isooctyl-4,4'-thio-bis(2-tertiary-butyl-5-methylphenyl)diphosphite, 2,2'-methylene-bis(4-methyl-6,1'-methyl cyclohexyl phenyl)polyphosphite, isooctyl-4,4'-isopropylidene-bisphenyl polyphosphite, 2-ethylhexyl-2,2'-methylene-bis(4-methyl-6,1'-methyl-cyclohexyl)phenyl triphosphite, tetra-tridecyl-4,4'-oxydiphenyl diphosphite, tetra-n-dodecyl-4,4'-n-butylidene bis(2-tertiary-butyl-5-methylphenyl)diphosphite, tetra-tridecyl-4,4'-isopropylidene bisphenyl diphosphite, hexa-tridecyl butane-1,1,3-tris(2'-methyl-5'-tertiary-butylphenyl-4')triphosphite.

Exemplary acid phosphites are di(phenyl)phosphite, monophenyl phosphite, mono(diphenyl)phosphite, dicresyl phosphite, di-(o-isooctylphenyl)phosphite, di(p-ethylhexylphenyl)phosphite, di(p-t-octylphenyl)phosphite, di(dimethylphenyl)phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl)phosphite, monocyclohexyl phosphite, dicyclohexyl phosphite, di(2-cyclohexyl phenyl)phosphite, di-α-naphthyl phosphite, diphenyl phenyl phosphite, di(diphenyl)phosphite, di-(2-phenyl ethyl)phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methylphenyl))-phosphite, (4,4'-thio-bis(2-tertiary-butyl-5-methylphenol))phenol phosphite, bis(4,4'-n-butylidene-bis(2-tertiary-butyl-5-methylphenol))phosphite, mono(4,4'-benzylidene-bis(2-tertiary-butyl-5-methylphenol))-phosphite, mono(2,2'-bis-(parahydroxyphenyl)-propane)phosphite, mono(4,4'-butylidene-bis(2-tertiary-butyl-5-methylphenol)phosphite, bis(4,4'-thio-bis(2-tertiary-butyl-5-methylphenol))phosphite, mono-2-ethylhexyl-mono-2,2'-methylene-bis(4-methyl-6,1'-methyl-cyclohexyl)phenol phosphite, bis(2,2'-bis(para-hydroxyphenyl)propane)phosphite, monoisooctylmono(4,4'-thio-bis(2-tertiary-butyl-5-methylphenol))phosphite, isooctyl-(2,6-bis(2'-hydroxy-3,5-dinonylbenzyl)-4-nonylphenyl))phosphite, tri-tridecyl-4,4'-n-butylidene-bis(2-tertiary-butyl-5-methylphenyl)diphosphite, trii-sooctyl-4,4'-thio-bis(2-tertiary-butyl-5-methylphenyl)-diphosphite, bis(2,2'-methylenebis(4-methyl-6,1'-methyl cyclohexyl phenyl))phosphite, isooctyl-4,4'-isopropylidene-bis-phenyl phosphite, monophenyl mono(2,2'-methylene-bis(4-methyl-6,1'-methyl-cyclohexyl))triphosphite, di-tridecyl-4,4'-oxydiphenyl diphosphite, di-n-dodecyl-4,4'-n-butylidene-bis(2-tertiary-butyl-5-methylphenyl)diphosphite, di-tridecyl-4,4'-isopropylidene bisphenyl diphosphite, tetra-tridecyl butane-1,1,3-tris(2'-methyl-5-tertiary-butylphenyl-4)-triphosphite.

The thiodipropionic acid ester has the following formula:

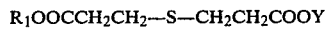

in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

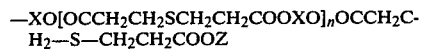

where Z is hydrogen, $R_2$ or M, n is the number of thiodipropionic acid ester units in the chain, and X is a bivalent hydrocarbon group of the type of $R_1$, that is, alkylene, alkenylene, cycloalkylene, mixed alkylene-arylene and mixed alkylenecycloalkylene radicals; hydroxyalkylene and hydroxyalkyloxyalkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the Periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming within the above-designated categories within the general formula can be defined as follows:

(a) $R_1OOCCH_2CH_2SCH_2CH_2COOH$
(b) $R_1OOCH_2CH_2SCH_2CH_2COOR_2$
(c) $R_1O[OCCH_2CH_2SCH_2CH_2COOX-O]-{}_nOCCH_2CH_2SCH_2CH_2COOZ$
(d) $R_1OOCCH_2CH_2SCH_2CH_2COOM$

In the above formulae $R_1$ and $R_2$, M, X and Z are the same as before and the value of $n_1$ can range upwards from 1, but there is not upper limit on $n_1$ except as is imposed by the ratio of cabon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, $R_2$ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric acid valeric acids.

Typical X radicals are alkylene radicals such as ethylene, tetramethylene, hexamethylene, decamethylene, alkyl-substituted alkylene radicals such as 1,2-propylene, $$-CH_2-\underset{\underset{CH_3}{|}}{\overset{\overset{CH_3}{|}}{C}}- \text{ and } -CH_2-\underset{\underset{CH_3}{|}}{\overset{\overset{CH_3}{|}}{C}}-CH_2-$$

arylene radicals such as phenylene methylenephenylene —CH$_2$— dimethylene phenylene —CH$_2$—⟨⟩—CH$_2$— and alicyclylene such as cyclohexylene and cyclopentylene

As exemplary of the thiodipropionic acid esters which can be used, there can be mentioned the following: monolauryl thiodipropionic acid, dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl)thiodipropionic acid.

These esters are for the most part known compounds, but where they are not available, they are readily prepared by esterification of thiodipropionic acid and the corresponding alcohol.

Also useful are:

(1) Thioalkanoic acid amides of Tokuno et al Japanese Pat. No. 16,286/68 having the formula:

$$R_1-S-R_2-CONH-\underset{R}{\underset{|}{\text{⟨⟩}}}-OH$$ (with R substituents)

R is alkyl of one to eight carbon atoms, R$_1$ is alkyl of six to twenty-four carbon atoms, and R$_2$ is alkylene of one to six carbon atoms.

(2) Thioalkanoic acid amides of 1,3,5-triazines of Ozeki et al Japanese Pat. No. 20,366/68 having the formula:

$$R-S-C_2H_4-\underset{\underset{O}{\|}}{C}-N\begin{cases} N-\underset{\underset{O}{\|}}{C}-C_2H_4-S-R \\ N-\underset{\underset{O}{\|}}{C}-C_2H_4-S-R \end{cases}$$

R is alkyl of eight to eighteen carbon atoms.

(3) Bis-thioalkanoic acid amides of Yamamoto et al Japanese Pat. No. 23,765/68 having the formula:

$$R-S-C_2H_4-\underset{\underset{O}{\|}}{C}-NH-NH-\underset{\underset{O}{\|}}{C}-C_2H_4-S-R$$

R is alkyl of more than six carbon atoms, aryl or aralkyl.

(4) Bis-thioalkylanoic acid amides of Ozeki et al Japanese Pat. No. 26,184/69 having the formula:

$$R-S-C_2H_4-\underset{\underset{O}{\|}}{C}-NH-NH-\underset{\underset{O}{\|}}{C}-R_1-\underset{\underset{O}{\|}}{C}-NH-NH-\underset{\underset{O}{\|}}{C}-C_2H_4-S-R$$

R is alkyl of twelve to eighteen carbon atoms, and R$_1$ is alkylene of one to ten cabon atoms, cycloalkylene, or arylene.

(5) Bis-alkylene thioalkanoic acid amides of Ozeki Japanese Pat. No. 31,464/69 having the formula:

$$R-S-C_2H_4-\underset{\underset{O}{\|}}{C}-NH-CH_2-NH-\underset{\underset{O}{\|}}{C}-C_2H_4-S-R$$

R is alkyl of more than six carbon atoms, aryl, or aralkyl.

(6) Thioalkanoic acid amide derivatives of Minagawa et al, published Japanese application No. 106,484/74 having the formula:

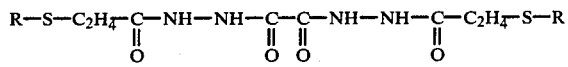

R is hydrocarbyl of one to twenty carbon atoms.

(7) Alkylene bis-thioalkanoic acid amides of U.S. Pat. No. 4,279,805 to Ohzeki et al, patented July 21, 1981, having the general formula:

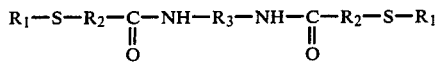

wherein:
$R_1$ is alkyl having from one to about fifty carbon atoms;
$R_2$ is alkylene having from one to about three carbon atoms; and
R is alkylene having from about two to about twelve carbon atoms.

β-Alkylthiopropionic acid esters having the general formula:

wherein:
R is alkyl of four to twenty carbon atoms;
n is a number from 1 to 6; and
R' is the residue of an alcohol having from one to six hydroxyl groups.

Pentaerythritol tetra dodecyl thio propionate is an example of this group.

Other conventional light stabilizers can be employed, such as hydroxybenzophenones such as 2-hydroxy-4-methoxybenzophenone, 2-hydroxy-4-n-octoxy benzophenone, 2,4-dihydroxybenzophenone, benzotriazoles, such as 2(2-hydroxy-5-methylphenyl)benzotriazoles, 2(2-hydroxy-3-t-butyl-5-methylphenyl)-5-chlorobenzotriazole, 2(2-hydroxy- 3-5-di-t-butylphenyl)5-chlorobenzotriazole, 2(2-hydroxy-3,5-di-t-amylphenyl)-benzotriazole, benzoates such as phenylsalicylate, 2,4-di-t-butylphenyl-3,5-di-t-butyl-4-hydroxy phenylbenzoate, nickel compounds such as nickel-2,2'-thiobis(4-t-octyl-phenolate), nickel-monoethyl(3,5-di-t-butyl-4-hydroxybenzyl)phosphonate, substituted acrylonitriles such as methyl-α-cyano-β-methyl-β-(p-methoxy phenyl)acrylate and oxalic anilides such as N-2-ethyl phenyl-N'-2-ethoxy-5-t-butyl phenyl oxalic diamide, N-2-ethyl phenyl-N'-2-ethoxy phenyl oxalic diamide.

A sufficient amount of the stabilizer or combination is used to improve the resistance of the synthetic polymer to deterioration in physical properties when exposed to heat and light, including, for example, discoloration, reduction in melt viscosity and embrittlement. Very small amounts are usually adequate. Amounts within the range from about 0.001 to about 5% total stabilizers including the polymeric light stabilizer of the invention by weight of the polymer are satisfactory. Preferably, from 0.01 to 3% is employed for optimum stabilization.

Inasmuch as the mixed light stabilizers of the invention are liquids, the stabilizers are readily rendered in liquid, comprising a blend of:

(a) mixed light stabilizer in an amount of from about 10 to about 35 parts by weight;
and optionally:

(b) a phenolic antioxidant (preferably liquid) in an amount from about 10 to about 35 parts by weight; and/or (c) other heat or light stabilizers (preferably liquid) in an amount of from about 10 to about 35 parts by weight.

The mixed light stabilizer of the invention can be employed in combination with phenolic antioxidant and/or other conventional heat and light stabilizers for the particular synthetic polymer.

Thus, for example, in the case of polyvinyl chloride resins, other polyvinyl chloride resin heat stabilizers can be included, including polyvalent and metal fatty acid salts such as barium and cadmium salts of the higher fatty acids; organotin compounds; and epoxy compounds.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylontrile-butadienestyrene terpolymers, other antioxidants and polyvalent metal salts of the higher fatty acids can be used.

In addition, other conventional additives for synthetic polymers, such as plasticizers, lubricants, emulsifiers, antistatic agents, flame-proofing agents, pigments and fillers, can be employed.

The stabilizer or combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following examples represent preferred embodiments of synthetic resin compositions in accordance with the invention.

EXAMPLES 1 TO 11

Polypropylene compositions were prepared using stabilizers of the invention and four of the prior art, and having the following formulation:

| Ingredient | Parts by Weight |
| --- | --- |
| Polypropylene | 100 |
| Tris(3,5-di-t-butylbenzyl) isocyanurate | 0.2 |
| Stabilizer as shown in Table I | 0.3 |

The compositions were thoroughly blended in a Brabender Plastograph, and then compression-molded to form sheets 0.3 mm thick. Pieces 2.5 cm² were cut off from the sheets and exposed to a high voltage mercury lamp and with and without immersion in hot water at 80° C. for 20 hours. The hours to failure were noted and the results are shown in Table I.

TABLE I

| | Stabilizer | Hours to Failure Without Immersion | Hours to Failure After Immersion for 20 hours | % Retention of light stability |
|---|---|---|---|---|
| Control 1 | Tetrakis(2,2,6,6-tetramethyl-4-piperidyl) butane-1,2,3,4-tetracarboxylate | 750 | 490 | 65 |
| Control 2 | Mono stearyl-tris(2,2,6,6-tetramethyl-4-piperidyl) butane-1,2,3,4-tetracarboxylate | 530 | 480 | 91 |
| Control 3 | Tris(2,2,6,6-tetramethyl-4-piperidyl) butane-1,2,3-tricarboxylate | 620 | 410 | 66 |
| Control 4 | Bis(2,2,6,6-tetramethyl-4-piperidyl) sebacate | 450 | 290 | 64 |
| Example 1 | 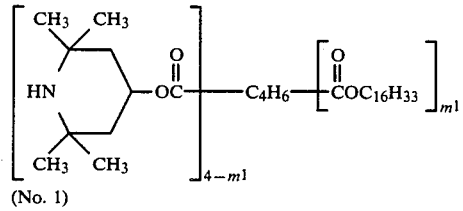 (No. 1) | 740 | 670 | 91 |
| Example 2 | 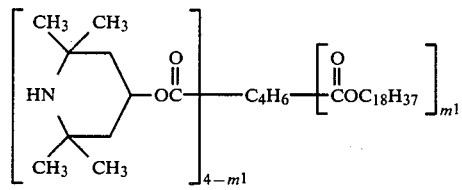 (No. 2) | 740 | 680 | 92 |
| Example 3 | 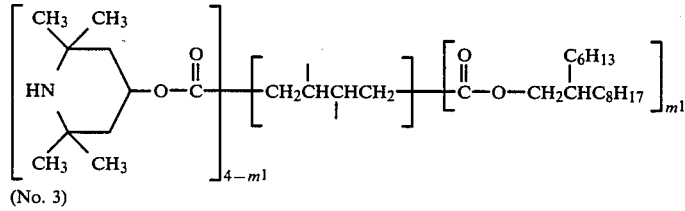 (No. 3) | 720 | 660 | 92 |
| Example 4 | 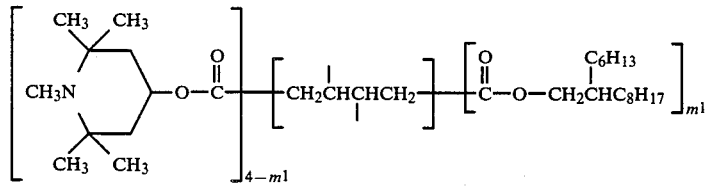 (No. 4) | 740 | 670 | 91 |
| Example 5 | 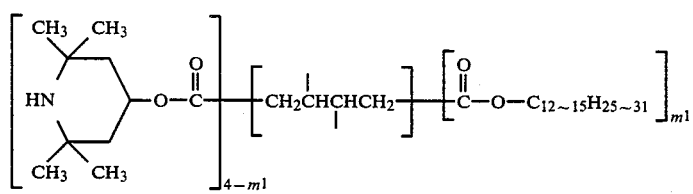 (No. 7) | 710 | 650 | 92 |
| Example 6 | 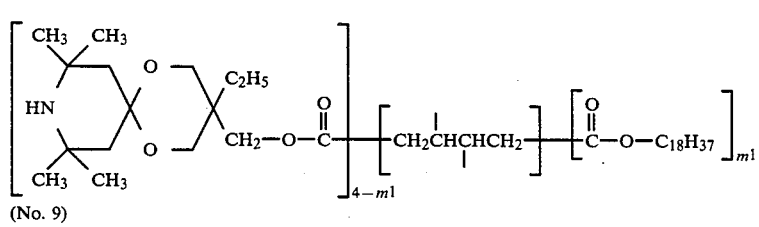 (No. 9) | 700 | 630 | 90 |

TABLE I-continued

| Stabilizer | Hours to Failure Without Immersion | Hours to Failure After Immersion for 20 hours | % Retention of light stability |
|---|---|---|---|
| Example 7 (No. 10): [HN-piperidine(tetramethyl)-O-C(=O)-[CH$_2$CHCHCH$_3$]-[C(=O)-O-C$_{13}$H$_{27}$(iso)]$_{m1}$]$_{4-m1}$ | 610 | 570 | 93 |
| Example 8 (No. 12): [HN-piperidine(tetramethyl)-O-C(=O)-[(CH$_2$)$_5$(CH)$_4$(CH$_2$)$_5$]-[C(=O)-O-C$_{18}$H$_{37}$]$_{m1}$]$_{4-m1}$ | 710 | 660 | 93 |
| Example 9 (No. 13): [CH$_3$N-piperidine(tetramethyl)-O-C(=O)-[N-(CH$_2$)$_3$]-[C(=O)-O-CH$_2$-CHC$_8$H$_{17}$(C$_6$H$_{13}$)]$_{m1}$]$_{4-m1}$ | 730 | 640 | 88 |
| Example 10 (No. 14): [HN-piperidine(tetramethyl)-OC(=O)-C$_4$H$_6$-[CNH-C$_{18}$H$_{37}$]$_{m1}$]$_{4-m1}$ | 700 | 600 | 86 |
| Example 11 (No. 16): [CH$_3$N-piperidine(tetramethyl)-OC(=O)-C$_4$H$_6$-[COC$_{13}$H$_{27}$-iso]$_{m1}$]$_{4-m1}$ | 750 | 680 | 91 |

The superiority of the stabilizers of the invention is apparent from the above data.

EXAMPLES 12 TO 18

High density polyethylene compositions were prepared using the stabilizers of the invention and three of the prior art, and having the following formulation:

| Ingredient | Parts by Weight |
|---|---|
| High-density polyethylene | 100 |
| Ca stearate | 1 |
| Tetrakis-(methylene-3-(3,5-di-t-butyl-4-hydroxyphenyl) propionate) methane | 0.1 |
| Distearylthiodipropionate | 0.3 |
| Stabilizer as shown in Table II | 0.2 |

The stabilizer was blended with the polymer on a two-roll mill and sheets 0.5 mm thick were prepared by compression-molding of the blend. Pieces 2.5 cm square were cut off from the sheets, and exposed to a high voltage mercury lamp and with and without immersion in hot water at 80° C. for twenty hours. The time in hours when degradation set in, as determined by a significant discoloration and/or embrittlement, was noted as hours to failure, and the results are reported in Table II.

TABLE II

| | Stabilizer | Hours to Failure Without Immersion | Hours to Failure After Immersion for 20 hours | % Retention of light stability |
|---|---|---|---|---|
| Control 1 | Tetrakis(2,2,6,6-tetramethyl-4-piperidyl)butane-1,2,3,4-tetra-carboxylate | 1250 | 940 | 75 |
| Control 2 | Monostearyl-tris(2,2,6,6-tetramethyl-4-piperidyl)butane-1,2,3,4-tetracarboxylate | 1020 | 920 | 90 |
| Control 3 | Dimethyl-bis(2,2,6,6-tetramethyl-4-piperidyl)butane-1,2,3,4-tetracarboxylate | 940 | 710 | 76 |
| Example 12 | 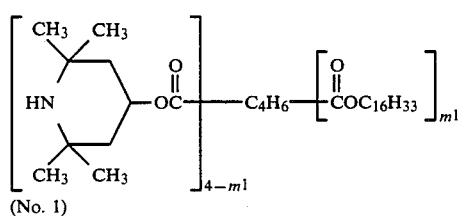 (No. 1) | 1250 | 1130 | 90 |
| Example 13 | 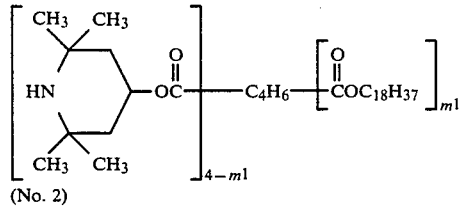 (No. 2) | 1220 | 1090 | 89 |
| Example 14 | 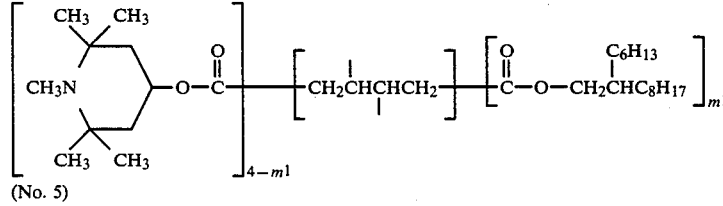 (No. 5) | 1210 | 1100 | 91 |
| Example 15 | 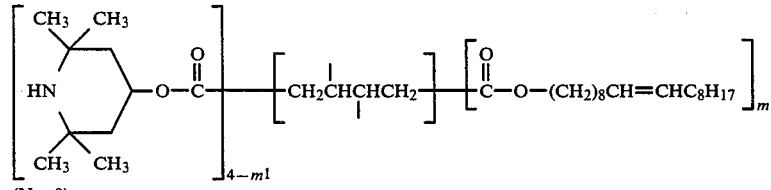 (No. 8) | 1240 | 1110 | 90 |
| Example 16 | 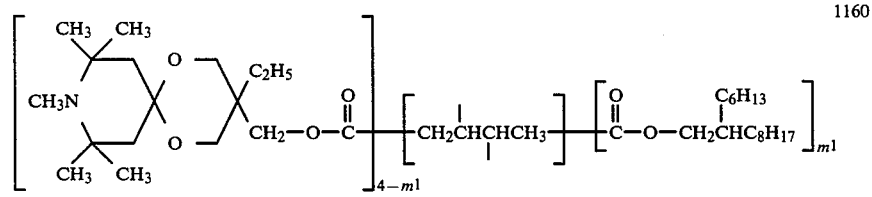 (No. 11) | 1160 | 1020 | 88 |
| Example 17 | 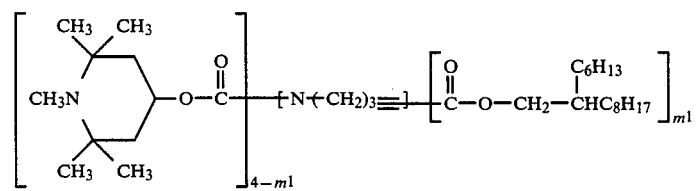 (No. 13) | 1120 | 980 | 88 |

TABLE II-continued

| Stabilizer | Hours to Failure Without Immersion | After Immersion for 20 hours | % Retention of light stability |
|---|---|---|---|
| Example 18 (No.15) 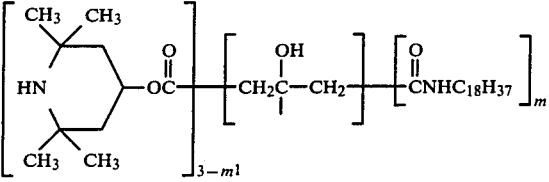 | 1100 | 970 | 88 |

The superiority of the stabilizers of the invention is apparent from the above data.

EXAMPLES 19 TO 28

A group of polyvinyl chloride resin compositions was prepared having the following formulation:

| Ingredient | Parts by Weight |
|---|---|
| Polyvinyl chloride | 100 |
| Dioctylphthalate | 48 |
| Epoxidized soybean oil | 2 |
| Tris(nonyl phenyl) phosphite | 0.2 |
| Ca stearate | 1.0 |
| Zn stearate | 0.1 |
| Stabilizer as shown in Table III | 0.3 |

This formulation was blended and sheeted off on a two-roll mill to form sheets 1 mm thick. Strips 1 cm wide were cut off from the sheets, and exposed to a high voltage mercury lamp and with and without immersion in hot water at 80° C. for twelve hours. The time in hours was then noted for the sheets to develop a noticeable discoloration and/or embrittlement, indicating deterioration due to oxidation in the presence of ultraviolet light. The following results were obtained:

TABLE III

| | Stabilizer | Hours to Failure Without Immersion | After Immersion for 20 hours | % Retention of light stability |
|---|---|---|---|---|
| Control 1 | Tetrakis(2,2,6,6-tetramethyl-4-piperidyl) butane-1,2,3,4-tetracarboxylate | 720 | 490 | 68 |
| Control 2 | Mono stearyl-tris(2,2,6,6-tetramethyl-4-piperidyl) butane-1,2,3,4-tetracarboxylate | 550 | 420 | 76 |
| Control 3 | Tris(2,2,6,6-tetramethyl-4-piperidyl) nitrilotriacetate | 820 | 490 | 60 |
| Example 19 | (No. 2) | 710 | 580 | 82 |
| Example 20 | (No. 3) | 660 | 560 | 85 |
| Example 21 | (No. 4) | 680 | 550 | 81 |

TABLE III-continued

| | | Hours to Failure | | |
|---|---|---|---|---|
| | Stabilizer | Without Immersion | After Immersion for 20 hours | % Retention of light stability |
| Example 22 | ![structure No. 6]: piperidine(2,2,6,6-tetramethyl, HN)–O–C(=O)–[CH$_2$CHCHCH$_2$]$_{4-m1}$–[C(=O)–O–C$_{13}$H$_{27}$(iso)]$_{m1}$ (No. 6) | 680 | 540 | 79 |
| Example 23 | ![structure No. 9]: piperidine(2,2,6,6-tetramethyl, HN) spiro-dioxy–CH$_2$–O–C(=O)–[CH$_2$CHCHCH$_2$]$_{4-m1}$–[C(=O)–O–C$_{18}$H$_{37}$]$_{m1}$, with C$_2$H$_5$ branch (No. 9) | 700 | 580 | 83 |
| Example 24 | ![structure No. 10]: piperidine(2,2,6,6-tetramethyl, HN)–O–C(=O)–[CH$_2$CHCHCH$_3$]$_{4-m1}$–[C(=O)–O–C$_{13}$H$_{27}$(iso)]$_{m1}$ (No. 10) | 630 | 500 | 79 |
| Example 25 | ![structure No. 12]: piperidine(2,2,6,6-tetramethyl, HN)–O–C(=O)–[(CH$_2$)$_5$(CH)$_4$(CH$_2$)$_5$]$_{4-m1}$–[C(=O)–O–C$_{18}$H$_{37}$]$_{m1}$ (No. 12) | 660 | 550 | 83 |
| Example 26 | ![structure No. 13]: piperidine(2,2,6,6-tetramethyl, CH$_3$N)–O–C(=O)–[N(CH$_2$)$_3$]$_{4-m1}$≡[–C(=O)–O–CH$_2$–CH(C$_6$H$_{13}$)C$_8$H$_{17}$]$_{m1}$ (No. 13) | 790 | 630 | 80 |
| Example 27 | ![structure No. 14]: piperidine(2,2,6,6-tetramethyl, HN)–O–C(=O)–[C$_4$H$_6$]$_{4-m1}$–[C(=O)NH–C$_{18}$H$_{37}$]$_{m1}$ (No. 14) | 650 | 510 | 78 |

TABLE III-continued

|  | Hours to Failure | | |
|---|---|---|---|
| Stabilizer | Without Immersion | After Immersion for 20 hours | % Retention of light stability |
| Example 28 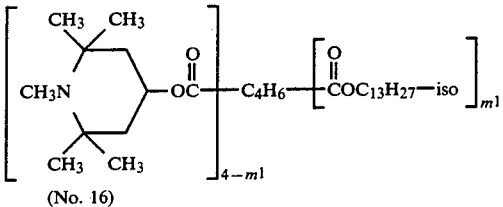 (No. 16) | 720 | 580 | 81 |

The superiority of the stabilizers of the invention is apparent from the above data.

EXAMPLES 29 TO 36

Acrylonitrile-butadiene-styrene terpolymer resin compositions were prepared using stabilizers of the invention and four of the prior art, and having the following formulations:

| Ingredient | Parts by Weight |
|---|---|
| Acrylonitrile-butadiene-styrene terpolymer | 100 |
| 4,4′-Butylidene-bis(2-t-butyl-m-cresol) | 0.1 |
| Stabilizer as shown in Table IV | 0.3 |

The stabilizer was blended with the resin on a two-roll mill, and sheets 3 mm thick were prepared by compression molding of the resulting blend. Pieces 2.5 cm square were cut off from the sheets, and exposed to a high voltage mercury lamp for 800 hours and with and without immersion in hot water at 80° C. for twenty hours. Tensile strength before and after the test was determined, and the results reported as the percent of tensile strength retained, at the end of this time, in Table IV.

TABLE IV

|  | Stabilizer | % Retention of Tensile Strength | |
|---|---|---|---|
|  |  | Without Immersion | After Immersion for 20 Hours |
| Control 1 | Tetrakis(2,2,6,6-tetramethyl-4-piperidyl)butane-1,2,3,4-tetracarboxylate | 90 | 74 |
| Control 2 | Mono stearyl-tris(2,2,6,6-tetramethyl-4-piperidyl)butane-1,2,3,4-tetracarboxylate | 72 | 64 |
| Control 3 | Hexa(2,2,6,6-tetramethyl-4-piperidyl)tetradecane-1,6,7,8,9,14-hexacarboxylate | 86 | 66 |
| Control 4 | Bis(,2,26,6-tetramethyl-4-piperidyl)sebacate | 69 | 50 |
| Example 29 | 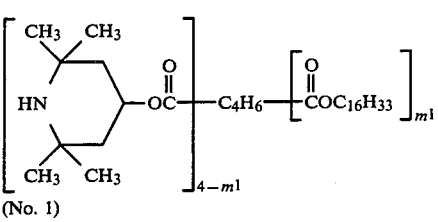 (No. 1) | 88 | 83 |
| Example 30 | 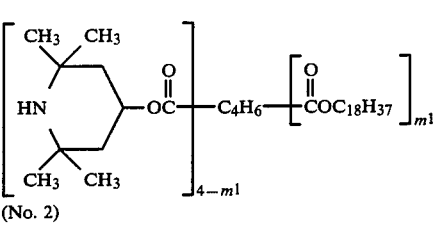 (No. 2) | 90 | 84 |
| Example 31 | 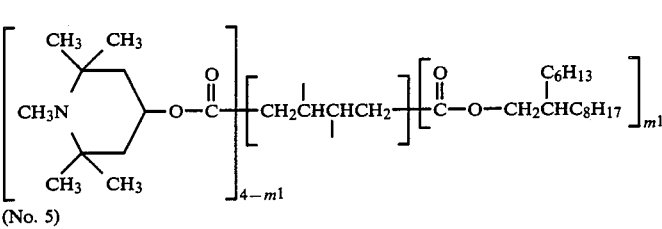 (No. 5) | 86 | 83 |

TABLE IV-continued

| Stabilizer | % Retention of Tensile Strength Without Immersion | After Immersion for 20 Hours |
|---|---|---|
| Example 32 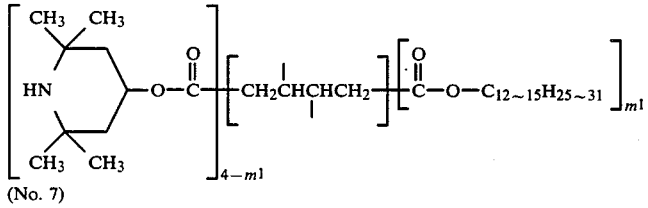 (No. 7) | 88 | 82 |
| Example 33 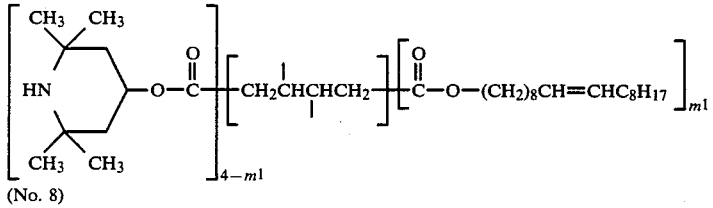 (No. 8) | 87 | 82 |
| Example 34 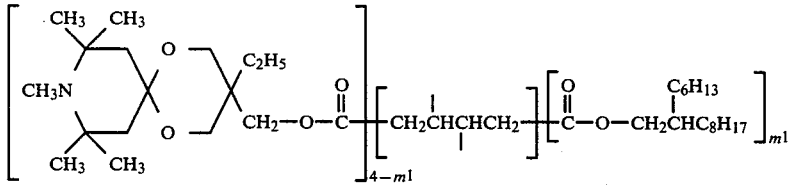 (No. 11) | 85 | 80 |
| Example 35 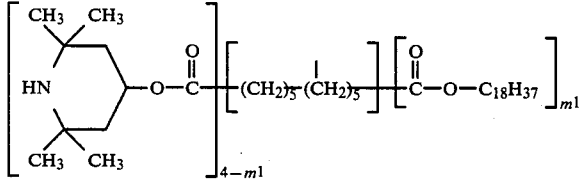 (No. 12) | 85 | 81 |
| Example 36 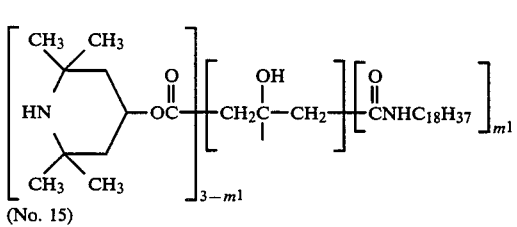 (No. 15) | 84 | 79 |

The superiority of the stabilizers of the invention is apparent from the above data.

EXAMPLES 37 TO 44

Polyurethane resin compositions were prepared using stabilizers of the invention and having the following formulation:

| Ingredient | Parts by Weight |
|---|---|
| Polyurethane resin (Asahi Denka U-100)[1] | 100 |
| Ca stearate | 0.7 |
| Zn stearate | 0.3 |
| 2,6-di-t-butyl-p-cresol | 0.1 |
| Stabilizer as shown in Table V | 0.3 |

[1] A polyurethane-isocyanurate made from toluene diisocyanate and alkylene polyol.

The stabilizer was blended with the finely powdered polyurethane resin on a two-roll mill for five minutes at 70° C., and the sheet was then compression-molded at 120° C. for five minutes to form sheets 0.5 mm thick. Pieces 2.5 cm square were cut out from the sheets, and exposed to ultraviolet light in a Fade-O-Meter for thirty hours and with and without extraction with carbon tetrachloride for two hours. Elongation before and after exposure was determined, and the percent elongation retained after the exposure is given in Table V.

TABLE V
| | Stabilizer | % Retention of Elongation | |
|---|---|---|---|
| | | Without Extraction | After Extraction |
| Control 1 | Tetrakis(2,2,6,6-tetramethyl-4-piperidyl)butane-1,2,3,4-tetracarboxylate | 82 | 69 |
| Control 2 | Mono stearyl-tris(2,2,6,6-tetramethyl-4-piperidyl)butane-1,2,3,4-tetracarboxylate | 73 | 66 |
| Control 3 | Bis(,2,26,6-tetramethyl-4-piperidyl)adipate | 70 | 52 |
| Example 37 | 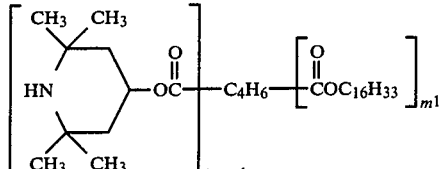 (No. 1) | 80 | 74 |
| Example 38 | 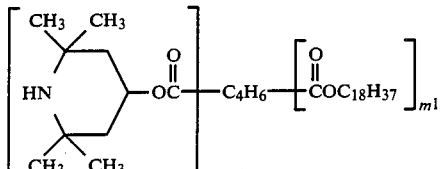 (No. 2) | 82 | 77 |
| Example 39 | 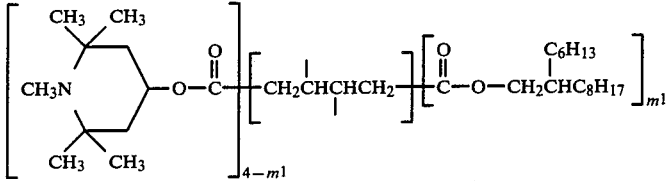 (No. 4) | 83 | 78 |
| Example 40 | 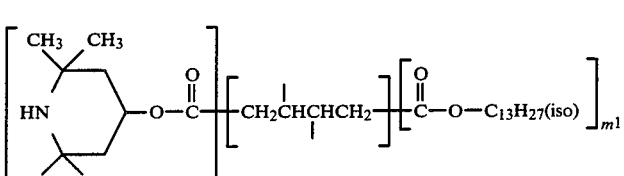 (No. 6) | 79 | 73 |
| Example 41 | 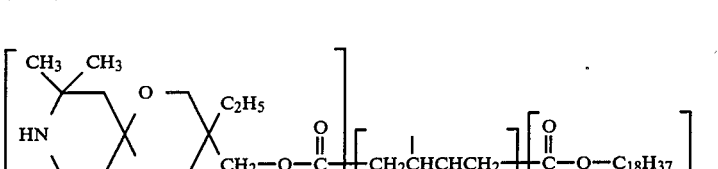 (No. 9) | 81 | 74 |
| Example 42 | 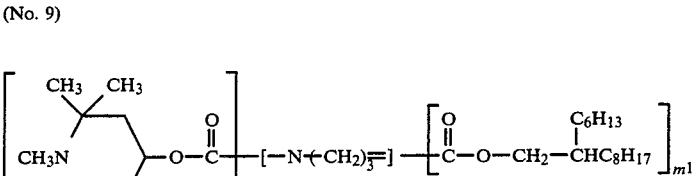 (No. 13) | 80 | 74 |

TABLE V-continued

| Stabilizer | % Retention of Elongation | |
|---|---|---|
| | Without Extraction | After Extraction |
| Example 43 $\left[\begin{array}{c}\text{CH}_3\;\;\text{CH}_3\\ \text{HN}\diagup\!\!\!\diagdown\!\!-\text{OC}\!\!-\!\!\text{C}_4\text{H}_6\!-\!\!\left[\!\!\begin{array}{c}\text{O}\\ \|\\ \text{CNH}\!-\!\text{C}_{18}\text{H}_{37}\end{array}\!\!\right]_{m1}\\ \text{CH}_3\;\;\text{CH}_3\end{array}\right]_{4-m1}$ (No. 14) | 77 | 72 |
| Example 44 $\left[\begin{array}{c}\text{CH}_3\;\;\text{CH}_3\\ \text{CH}_3\text{N}\diagup\!\!\!\diagdown\!\!-\text{OC}\!\!-\!\!\text{C}_4\text{H}_6\!-\!\!\left[\!\!\begin{array}{c}\text{O}\\ \|\\ \text{COC}_{13}\text{H}_{27}\!-\!\text{iso}\end{array}\!\!\right]_{m1}\\ \text{CH}_3\;\;\text{CH}_3\end{array}\right]_{4-m1}$ (No. 16) | 83 | 78 |

The superiority of the stabilizers of the invention is apparent from the above data.

EXAMPLES 45 TO 53

The stabilizers of this invention are effective as light stabilizers for coatings.

The effect of the stabilizer in a two-coat metallic effect finish comprising metallic effect priming lacquer and unpigmented finishing lacquer was determined.

(a) Metallic Effect Priming Lacquer

Methylmethacrylate 100 g, n-butylacrylate 66 g, 2-hydroxyethylmethacrylate 30 g, methacrylic acid 4 g, xylene 80 g and n-butanol 20 g were heated with stirring at 110° C. A solution of azo-bis(isobutyronitrile) 2 g, dodecyl mercaptan 0.5 g, xylene 80 g and n-butanol 20 g was then added dropwise over 3 hours. The solution was stirred an additional 2 hours at 110° C., thus obtaining an acrylic resin solution.

The above acrylic resin solution 12 parts, butoxylated methylol melamine (Mitsui-Toatsu Co., Yuban 20SE60; solids content 60%) 2.5 parts, cellulose acetobutyrate (20% butylacetate solution) 50 parts, aluminum pigment (Yoyo Aluminum Co., Alpaste 1123N) 5.5 parts, xylene 10 parts, butylacetate 20 parts and copper phthalocyanine blue 0.2 part were blended.

(b) Unpigmented Finishing Lacquer

The above acrylic resin solution 48 parts, butoxylated-methylol melamine 10 parts, xylene 10 parts, butoxyethylacetate 4 parts and stabilizer as shown in Table VI 0.15 part were blended.

Pieces of steel sheeting, which were coated with a primer, were first coated with the priming lacquer, and subsequently with the finishing lacquer. The priming lacquer was sprayed on to a thickness of about 20μ, and aired for 10 minutes. Then the clear lacquer was sprayed on to a thickness of about 30μ. After being aired 15 minutes, the samples were stoved for 30 minutes at 140° C. The samples were heated in a Fade-Meter with and without immersion in hot water at 80° C. for 24 hours. The time in hours when degradation set in, as determined by a cracking on a surface of the sheet, was noted as hours to failure, and the results are shown in Table VI.

TABLE VI

| | Stabilizer | Hours to Failure | |
|---|---|---|---|
| | | Immersion Immersion | After Immersion for 24 hours |
| Control 1 | Tetrakis(2,2,6,6-tetramethyl-4-piperidyl) butane-1,2,3,4-tetracarboxylate | 3500 | 2400 |
| Control 2 | Mono stearyl-tris(2,2,6,6-tetramethyl-4-piperidyl) butane-1,2,3,4-tetracarboxylate | 2700 | 2300 |
| Control 3 | Mixture of 85 wt. % of bis(1,2,2,6,6-penta methyl-4-piperidyl) sebacate and 15 wt. % of mono methyl-mono(1,2,2,6,6-pentamethyl-4-piperidyl) sebacate | 2800 | 1900 |
| Example 45 | $\left[\begin{array}{c}\text{CH}_3\;\;\text{CH}_3\\ \text{HN}\diagup\!\!\!\diagdown\!\!-\text{OC}\!\!-\!\!\text{C}_4\text{H}_6\!-\!\!\left[\!\!\begin{array}{c}\text{O}\\ \|\\ \text{COC}_{16}\text{H}_{33}\end{array}\!\!\right]_{m1}\\ \text{CH}_3\;\;\text{CH}_3\end{array}\right]_{4-m1}$ (No. 1) | 3400 | 2900 |

TABLE VI-continued
| Stabilizer | Hours to Failure | |
|---|---|---|
| | Immersion Immersion | After Immersion for 24 hours |
| Example 46 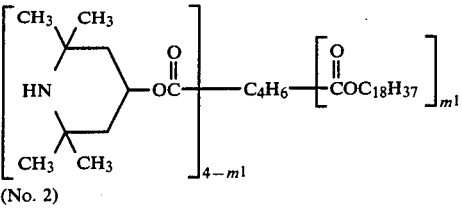 (No. 2) | 3200 | 2800 |
| Example 47 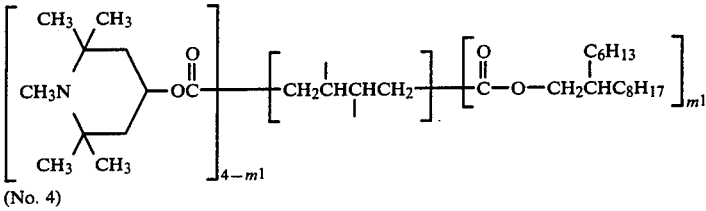 (No. 4) | 3700 | 3300 |
| Example 48 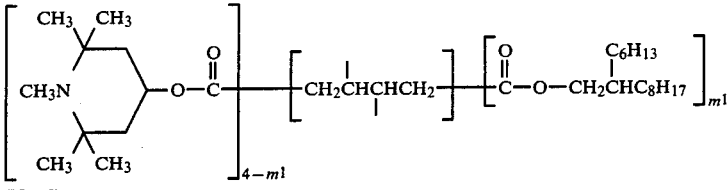 (No. 5) | 3500 | 3100 |
| Example 49 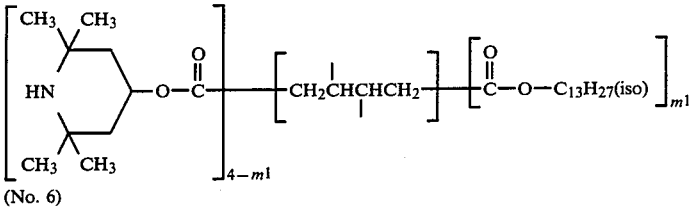 (No. 6) | 3200 | 2700 |
| Example 50 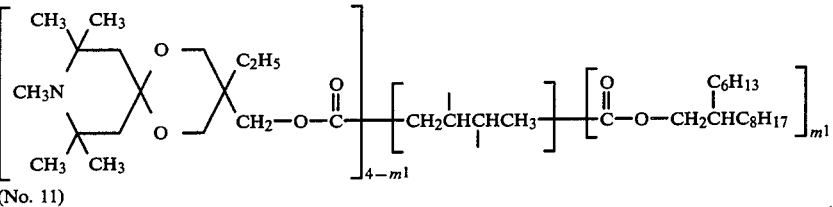 (No. 11) | 3000 | 2600 |
| Example 51 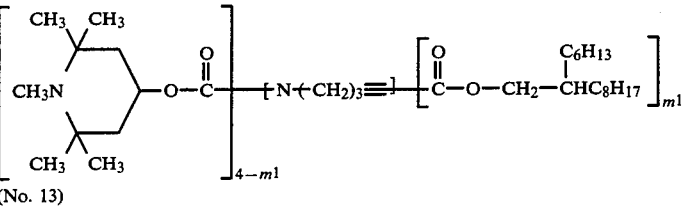 (No. 13) | 3100 | 2700 |
| Example 52 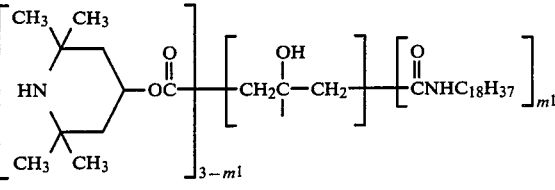 | 3000 | 2500 |

TABLE VI-continued

| | Hours to Failure | |
|---|---|---|
| Stabilizer | Immersion Immersion | After Immersion for 24 hours |
| (No. 15) | | |
| Example 53 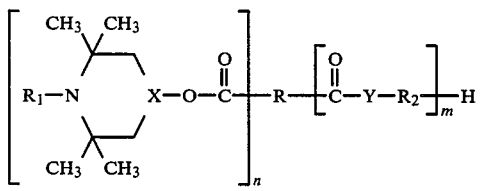 (No. 16) | 3700 | 3400 |

The superiority of the stabilizers of the invention is apparent from the above data.

Having regard to the foregoing disclosure, the following is claimed as the inventive and patentable embodiments thereof:

1. Mixed light stabilizers for synthetic polymers having the formula:

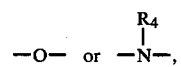

wherein:

R is a polyvalent group selected from the group consisting of aliphatic hydrocarbon groups having from one to about twenty carbon atoms, cycloaliphatic hydrocarbon groups having from three to about sixteen carbon atoms and aromatic hydrocarbon groups having from six to about thirty carbon atoms; such groups substituted with from one to about six groups selected from the group consisting of hydroxy, acyloxy, and halogen; and $N(C_{n1}H_{2n1})_3$ where $n_1$ is a number from one to five;

$R_1$ is selected from the group consisting of hydrogen, oxyl, alkyl, epoxy alkyl and hydroxy alkyl having from one to about twelve carbon atoms, alkyl aryl having from six to about eighteen carbon atoms, and acyl having from two to about twelve carbon atoms;

$R_2$ is selected from the group consisting of alkyl and alkenyl having from eight to about thirty carbon atoms;

$R_3$ is lower alkyl having from one to about six carbon atoms;

X is >CH— or

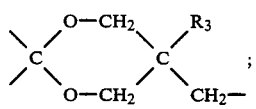

Y is

—O— or 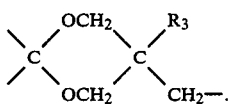

where $R_4$ is hydrogen or $R_2$;
m is a number from 0 to 6; and
n is a number from 3 to 6;
the mixture comprising from about 10 to about 60% by weight of compounds wherein m is 0, and from about 90 to about 40% by weight of compounds wherein m is from 1 to 6.

2. Mixed light stabilizers according to claim 1 in which R is aliphatic hydrocarbon.

3. Mixed light stabilizers according to claim 2 in which R is butylene.

4. Mixed light stabilizers according to claim 1 in which R is $N(CH_2)_3\equiv$.

5. Mixed light stabilizers according to claim 1 in which $R_1$ is hydrogen.

6. Mixed light stabilizers according to claim 1 in which $R_1$ is alkyl.

7. Mixed light stabilizers according to claim 1 in which $R_2$ is alkyl.

8. Mixed light stabilizers according to claim 1 in which $R_2$ is alkenyl.

9. Mixed light stabilizers according to claim 1 in which Y is O.

10. Mixed light stabilizers according to claim 1 in which X is >CH.

11. Mixed light stabilizers according to claim 1 in which X is

12. Mixed light stabilizers according to claim 1 in which n is 3.

13. Mixed light stabilizers according to claim 1 in which n is 4.

14. Mixed light stabilizers according to claim 1 in which n is 5.

15. Mixed light stabilizers according to claim 1 in which Y is $$-\overset{R_4}{\underset{|}{N}}-$$

where R₄ is hydrogen or R₂.

16. A polyvinyl chloride resin composition having improved resistance to deterioration when exposed to light, comprising a polyvinyl chloride resin formed at least in part of the recurring group:

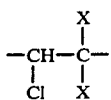

and having a chlorine content in excess of 49%, where X is either hydrogen or chlorine, and an amount sufficient to improve resistance to deterioration of the resin of a compound in accordance with claim 1.

17. A polyvinyl chloride resin composition in accordance with claim 16 in which the polyvinyl chloride resin is polyvinyl chloride homopolymer.

18. A polyvinyl chloride resin composition in accordance with claim 16 in which the polyvinyl chloride resin is a copolymer of vinyl chloride and vinyl acetate.

19. An olefin polymer composition having improved resistance to deterioration comprising an olefin polymer selected from the group consisting of polymers of alpha-olefins having from two to six carbon atoms and polystyrene, and an amount sufficient to improve resistance to deterioration of the resin of a compound in accordance with claim 1.

20. An olefin polymer composition in accordance with claim 19 wherein the polyolefin is polypropylene.

21. An olefin polymer composition in accordance with claim 19 wherein the polyolefin is polyethylene.

22. An olefin polymer composition in accordance with claim 19 wherein the polyolefin is ethylene-propylene copolymer.

23. An acrylonitrile-butadiene-styrene polymer having improved resistance to deterioration when exposed to light comprising an acrylonitrile-butadiene-styrene polymer and an amount sufficient to improve resistance to deterioration of the resin of a compound in accordance with claim 1.

24. A polyurethane resin composition having improved resistance to deterioration comprising a polyurethane resin and an amount sufficient to improve resistance to deterioration of the resin of a compound in accordance with claim 1.

* * * * *